[19] United States Patent
Angelucci et al.
[11] Patent Number: 5,037,970
[45] Date of Patent: Aug. 6, 1991

[54] 6-DEOXYANTHRACYCLINES

[75] Inventors: Francesco Angelucci; Sergio Penco; Ermes Vanotti, all of Milan; Federico Arcamone, Nerviano, all of Italy

[73] Assignee: Farmitalia Carlo Erba S.p.A., Milan, Italy

[21] Appl. No.: 501,869

[22] Filed: Mar. 28, 1990

Related U.S. Application Data

[62] Division of Ser. No. 622,177, Jun. 19, 1984, Pat. No. 4,939,282.

[30] Foreign Application Priority Data

Jun. 23, 1983 [GB] United Kingdom ................ 8317037

[51] Int. Cl.[5] ........................ C07H 15/24
[52] U.S. Cl. ........................ 536/6.4; 552/201
[58] Field of Search ........................ 552/201; 536/614

[56] References Cited

U.S. PATENT DOCUMENTS

| | | | |
|---|---|---|---|
| 4,046,878 | 9/1977 | Patelli et al. | 536/17 |
| 4,191,755 | 3/1980 | Masi et al. | 536/17 |
| 4,191,756 | 3/1980 | Masi et al. | 536/17 |
| 4,370,476 | 1/1983 | Usher | 536/113 |
| 4,465,671 | 8/1984 | Angelucci et al. | 536/6.4 |
| 4,939,282 | 7/1990 | Angelucci et al. | 552/206 |

FOREIGN PATENT DOCUMENTS

| | | |
|---|---|---|
| 2506772 | 12/1982 | France . |
| 2514754 | 4/1983 | France . |

OTHER PUBLICATIONS

The Journal of Organic Chemistry, vol. 48, No. 3, 1983, pp. 405–406, American Chemical Society; S. Penco: "Regiospecific total synthesis of 6-deoxyanthracyclines: 4-demethoxy-6-deoxydaunorubicin".
Tetrahedron, vol. 40, No. 22, 1984, pp. 4677–4683, Pergamon Press Ltd.; S. Penco et al.: "Regiospecific total synthesis of 6-deoxyanthracyclines".
Tetrahedron letters, vol. 22, No. 9, 1981, pp. 811–814, Pergamon Press Ltd., Oxford, GB; Jhillu Yaday et al.: "Regiospecific synthesis of (+)-deoxyanthracyclionones", pp. 811–813.
Chemical Abstracts, vol. 98, No. 7, Feb. 14, 193, No. 7, 2/14/83, No. 46929m; T. McCabe: "Structural studies of biologically interesting natural products".
Journal of the Chemical Society Chemical Communications, No. 8, 1984, pp. 530–531; Francesco Angelucci et al.: "Regiospecific total synthesis of 6-deoxyanthracyclines: 6-Deoxycarminomycin".

*Primary Examiner*—C. Warren Ivy
*Assistant Examiner*—Raymond Covington
*Attorney, Agent, or Firm*—Oblon, Spivak, McClelland, Maier & Neustadt

[57] ABSTRACT

A compound of the formula

XV

O OH O CH$_2$R$_1$ OH OH O O H$_3$C O R$_3$ NHX R$_2$ wherein R$_1$ represents a hydrogen atom or a hydroxy group, one of R$_2$ and R$_3$ represents a hydrogen atom, the other of R$_2$ and R$_3$ represents a hydrogen atom or a hydroxy group and X is a hydrogen atom or a trifluoro acetyl group. The N-trifluoroacetyl 7S:9S and 7R:9R derivatives of the $\alpha$-glycosides of formula XV can be separated by chromatography on silica gel to obtain, after mild alkaline hydrolysis the wanted 7S:9S $\alpha$-glycosides (R$_1$=H) as free bases and can eventually be transformed into their corresponding doxorubicin derivatives (R$_1$=OH) by known procedures.

2 Claims, No Drawings

6-DEOXYANTHRACYCLINES

This is a division of application Ser. No. 06/622,177, filed on June 19, 1984, now U.S. Pat. No. 4,939,282.

DESCRIPTION

The invention relates to a process for the preparation of 6-deoxy-anthracyclinones, to certain of the 6-deoxyanthracyclinones, to certain anthracycline glycosides prepared from them, to those anthracyclic glycosides in pharmaceutical compositions and to the preparation of those anthracycline glycosides.

The invention provides a process for the preparation of 6-deoxyanthracyclinones having the general formula I

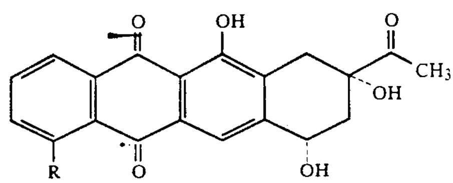

wherein R represents a hydrogen atom, a hydroxy group or a lower alkoxy group. The process, which is illustrated in the following reaction scheme, comprises (i) acetylating dimethyl 1,2,3,6-tetrahydro-phthalate (II) by treatment with acetic anhydride in the presence of tin tetrachloride, followed by treatment with a mild base or a mild acid (ii) reacting the resultant dimethyl 1,2,3,6-tetrahydro-4-acetyl-phthalate (III) with tosylhydrazine, (iii) reducing the resultant dimethyl 1,2,3,6-tetrahydro-4-(1-tosylhydrazone-ethyl)-phthalate (IV) with catechol borane and subsequently re-arranging the double bond from an endocyclic to an exocyclic position in the presence of sodium acetate, (iv) oxidizing the resultant 1,2-di-(methoxycarbonyl)-4-ethylidene-cyclohexane (V) with potassium permanganate and treating the resultant α-hydroxy-ketone with ethylene glycol in the presence of a catalytic amount of p-toluenesulphonic acid (v) condensing the resultant 2-methoxycarbonyl-5-[2-methyl-dioxolane-2-yl]-6-oxa-bicyclo[3,2,1]octan-7-one (VI) with a compound of the general formula VIII wherein R is as above defined (obtained by the action of an alkyllithium on a compound of the general formula VII wherein R is as above defined), (vi) opening the lactone ring and deprotecting the dioxolan protected keto group in the resultant compound of the general formula IX wherein R is as above defined by methanolysis, (vii) reducing the keto groups of the resultant compound of the general formula X wherein R is as above defined by treatment with a pyridine-borane complex in the presence of trifluoroacetic acid and converting the methoxycarbonyl group to a benzyloxycarbonyl group by treatment with phenyldiazomethane, (viii) esterifying the hydroxy groups and deesterifying the benzyloxycarbonyl group in the resultant compound of the general formula XI wherein R is as above defined by treatment with acetic anhydride in pyridine in the presence of 4-dimethylamino-pyridine followed by refluxing with cyclohexane in the presence of a palladium-on-carbon catalyst, (ix) cyclizing the resulting compound of the general formula XII wherein R′ represents a hydrogen atom, an acetoxy group or a lower alkoxy group by treatment with a mixture of trifluoroacetic anhydride and trifluoroacetic acid, and hydrolyzing the acetoxy groups with sodium methylate, (x) oxidizing the 1-hydroxyethyl group of the resultant compound of the general formula XIII wherein R is as above defined with silver carbonate, and oxidatively demethylating the resultant compound with aluminum trichloride in nitrobenzene, and (xi) protecting the 13-keto group of the resultant compound of the general formula XIV by treatment with ethylene glycol, brominating the resultant compound at C-7 by treatment in the presence of 2,2′-azo-bis-(isobutyronitrile) with bromine or N-bromosuccinimide, and hydrolysing the 7-bromo and 13-ketal groups.

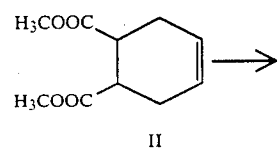

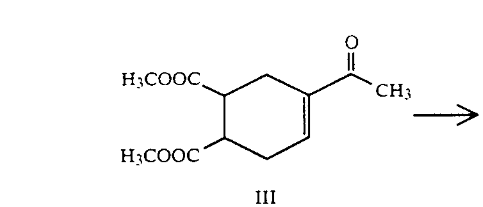

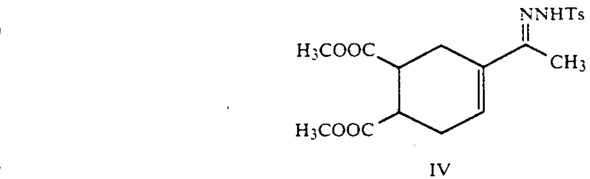

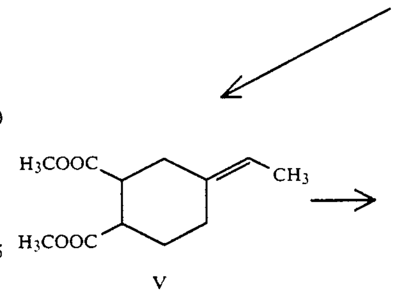

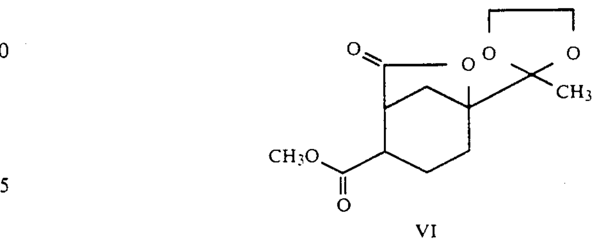

-continued

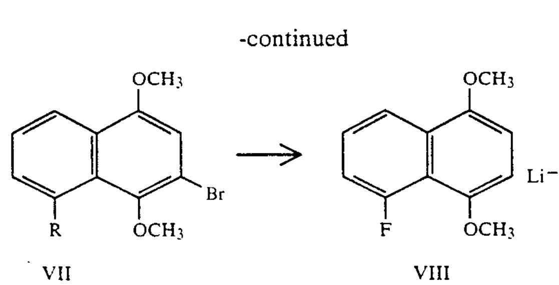

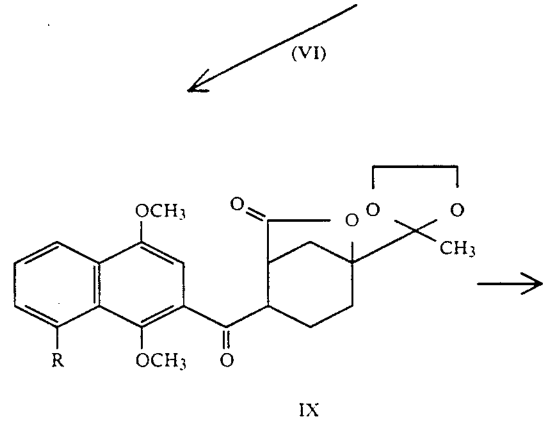

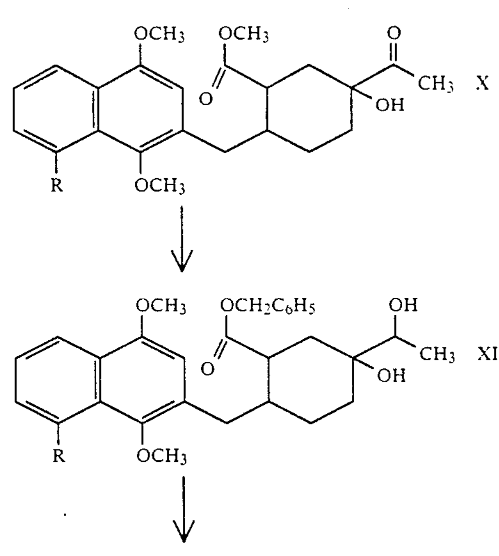

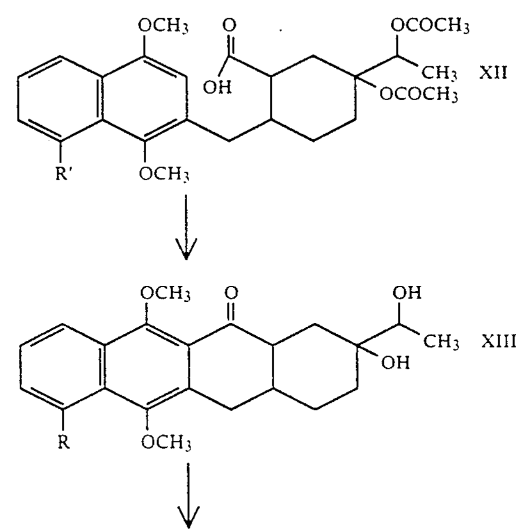

-continued

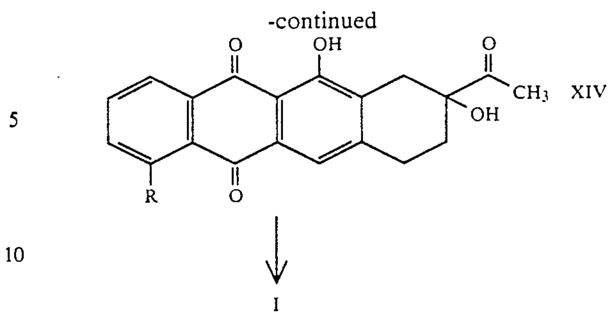

The starting compounds for the process according to the invention are known. 2-Bromo-1,4,5-trimethoxynaphthalene (VII, R=$OCH_3$) was described by R. L. Haman, R. B. Barber and H. Rapoport, J. Org. Chem., 44, 2153 (1979). The coupling reaction between the compounds VIII and VI proceeds regioselectively in high yield to give the key intermediate IX. The organometallic species affects only the carbonyl group of the methyl ester and not that of the lactone.

Step (xi) may be performed according to the method described by C. M. Wong et al., Can J. Chem., 51, 446 (1973), that is by bromination with bromine in the presence of 2,2'-azo-bis(isobutyronitrile) followed by hydrolysis of the 7-bromo-derivative and removal of the ketal group by acid treatment, or alternatively by bromination with N-bromo-succinimide in the presence of 2,2'-azo-bis(isobutyronitrile), by irradiation, treatment with silver acetate, hydrolysis of the ketal by acidic treatment and finally hydrolysis of the acetate with soduim methoxide.

The optical resolution of the compound IX may be carried out by the conventional method of conversion to diastereoisomeric derivatives using a chiral resolving agent. Resolution at this point enable (+)-4-demethoxy-6-deoxy-4- (R-substituted)-daunomycinones I to be obtained. The 6-deoxyanthracyclinones I, except that in which R represents a hydrogen atom, are novel and are included within the scope of the invention. 4-Demethoxy-6-deoxydaunomycinone, prepared by a different process, was described in our British Patent Specification No. 2100257. The present process is more efficient and more amenable to large scale production than the previous described process.

The invention also provides anthracyline glycosides having the general formula XV

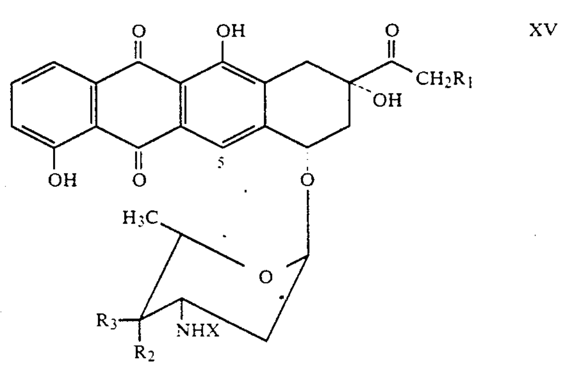

wherein $R_1$ represents a hydrogen atom or a hydroxy group, one of $R_2$ and $R_3$ represents a hydrogen atom, the other of $R_2$ and $R_3$ represents a hydrogen atom or a hydroxy group, and X represents a hydrogen atom or a trifluoroacetyl group, with the proviso that if X represents a trifluoroacetyl group than $R_1$ represents a hydrogen atom. These compounds may be named as follows:

XVa: $R_1=R_3=H$, $R_2=OH$, $X=COCF_3$, 4-demethyl-6-deoxy-N-trifluoroacetyl-daunorubicin.

XVb: $R_1=R_3=H$, $R_2=OH$, $X=H$, 4-demethyl-6-deoxy-daunorubicin.

XVc: $R_1=R_2=OH$, $R_3=H$, $X=H$, 4-demethyl-6-deoxy-doxorubicin.

XVd: $R_1=R_2=H$, $R_3=OH$, $X=COCF_3$, 4-demethyl-6-deoxy-N-trifluoroacetyl-4'-epi-daunorubicin XVe: $R_1=R_2=H$, $R_3=OH$, $X=H$, 4-demethyl-6-deoxy-4'-epi-daunorubicin XVf: $R_1=R_3=OH$, $R_2=H$, $X=H$, 4-demethyl-6-deoxy-4'-epi-doxorubicin XVg: $R_1=R_2=R_3=H$, $X=COCF_3$, 4-demethyl-6,4'-dideoxy-N-trifluoroacetyl-daunorubicin XVh: $R_1=R_2=R_3=X=H$, 4-demethyl-6,4'-dideoxy-daunorubicin XVi: $R_1=OH$, $R_2=R_3=X=H$, 4-demethyl-6,4'deoxy-doxorubicin.

These authracycline glycosides may be prepared from 4-demethyl-6-dexoy-daunomycinone (I, R=OH) by condensation thereof with a protected halosugar having the general formula XVI

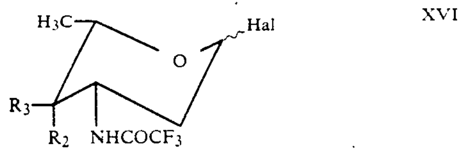

XVI wherein one of $R_2$ and $R_3$ represents a hydrogen atom and the other $R_2$ and $R_3$ represents a hydrogen atom or a trifluoroacetoxy group, and Hal represents a halogen atom, preferably a chlorine atom. This condensation proceeds in the presence of silver trifluoromethane sulphonate according to the method described in U.S. Pat. No. 4,107,423, giving an easily separable mixture of the 7S: 9S and 7R:9R O-trifluoroacetyl protected derivatives of the α-glycosides. XVa, XVd and XVg according to the halosugar XVI selected for the reaction.

The O-trifluoroacetyl group may be removed by methanolysis to give the compounds XVa, XVd and XVg which by mild alkaline hydrolysis can be converted to the glycosides XVb, XVe and XVh respectively. These, by 14-bromination and treatment with aqueous sodium formate in accordance with the method described in U.S. Pat. No. 3,803,124, give the corresponding doxorubicin derivatives XVc, XVf and XVi. These processes are within the scope of the invention.

The anthracycline glycosides XV have anti-tumor properties and accordingly the invention additionally provides a pharmaceutical composition comprising an anthracycline glycoside having the general formula XV or a pharmaceutically acceptable salt of such a glycoside in which X represents a hydrogen atom in admixture with a pharmaceutically acceptable diluent or carrier.

The invention is illustrated by the following Examples.

EXAMPLE 1

Dimethyl 1,2,3,6-tetrahydro-4-acetyl-phthalate (III)

10 g dimethyl 1,2,3,6-tetrahydro-phthalate (II) was treated at −5° C. with 25 ml of acetic anhydride in the presence of 9 ml of tin tetrachloride. The reaction mixture was poured into iced water and extracted with diethyl ether. The organic phase was washed with a saturated aqueous solution of sodium bicarbonate and then with water, and was then evaporated to dryness under vacuum. The obtained oil was dissolved in benzene, treated with a methanolic solution of hydrogen chloride. The solution was evaporated to dryness and the residue was purified by chromatography on column of silica gel to give 9 g of the title compound in 75% overall yield. mass spectrum: m/z 240 ($M^{+\cdot}$)

Ir (KBr): 1720 $cm^{-1}$ (C=O of ester); 1660 $cm^{-1}$ (C=O of α,β unsaturated ketone).

PMR ($CDCl_3$): inter alia δ 2.33 (s, $COCH_3$), 3.70 (s, —$COO\underline{CH}_3$) and 6.91 (m, $\underline{H}C$=C).

EXAMPLE 2

1,2-Di-(methoxycarbonyl)-4-ethylidene-cyclohexane (V)

17 g of dimethyl 1,2,3,6-tetrahydro-4-acetyl-phthalate, prepared as described in Example 1, was refluxed in anhydrous ethanol with 14.6 g of tosylhydrazine. After removal of the solvent, 24 g of dimethyl 1,2,3,6-tetrahydro-4-(1-tosylhydraaono-ethyl)-phthalate (IV) crystallized from water m.p. 162°-163° C. m/z 408 ($M^{+\cdot}$). This compound was dissolved in chloroform, and treated at 0° C. with 14 ml of catechol borane. Sodium acetate was added to the reaction mixture, which was then refluxed. After washing with water, the solvent was evaporated off and the residue was purified by chromatography on a column of silica gel giving 10 g of the title compound (yield 80%): m/z 226 ($M^{+\cdot}$); PMR ($CDCl_3$): inter alia δ 1.6 (d, J=8 Hz, $\underline{CH}_3$—CH=), 5.3 (q, J=8 Hz, $CH_3$—$\underline{CH}$=).

EXAMPLE 3

2-Methoxycarbonyl-5-(2-methyldioxolan-2-yl)-6-oxabicyclo[3,2,1]octan-7-one (VI)

8 g of 1,2-di-(methoxycarbonyl)-4-ethylidene-cyclohexane, prepared as described in Example 2, was dissolved in aqueous acetone containing 4.8 ml of acetic acid. An aqueous solution of potassium permanganate was added, and the mixture was allowed to stand for 60 minutes at room temperature. The excess oxidant was then destroyed and the reaction mixture, diluted with water, was extracted with ethyl acetate. The organic phase, washed with water and dried over anhydrous sodium sulphate, was evaporated to dryness under vacuum. The residue (9 g) was dissolved in benzene and refluxed for 60 minutes in the presence of a catalytic amount of p-toluenesulphonic acid. 4 ml of ethylene glycol was added and the reaction mixture was refluxed for a further 2 hours. After conventional work-up, the residue, obtained by evaporating off the solvent, was purified by chromatography on a column of silica gel using as eluent a toluene:acetone mixture (15:1 by volume). 3.0 g of the title compound was isolated (yield 33%): m.p. 69°-71° C.; m/z 271 ($MH^{+\cdot}$).

IR (KBr): 1790 $cm^{-1}$ (C=O five membered ring lactone) 1735 $cm^{-1}$ (C=O ester); 1720 $cm^{-1}$ (C=O ketone).

PMR ($CDCl_3$): inter alia 1.25 (s, $\underline{CH}_3$), 3.65 (s, $COO\underline{CH}_3$), and 3.9 (s, —O—$\underline{CH}_2$—$\underline{CH}_2$—O—).

EXAMPLE 4

2-(1,4,5-Trimethoxy-3-naphthylcarbonyl)-5-(2-methyl-dioxolan-2-yl)-6-oxa-bicyclo[3,2,1]octan-7-one (IX, R=$OCH_3$)

7 ml of a 1.65M hexane solution of n-butyllithium was dissolved in 30 ml of anhydrous tetrahydrofuran. To the solution was added at −78° C. a solution of 3.3 g of 1,4,5-trimethoxy-3bromo-naphthalene (VI, R=$OCH_3$) in 30 ml of anhydrous tetrahydrofuran. 2.5 g of 2-methoxycarbonyl-5-(2-methyl-dioxolan-2-yl)-6-oxa-bicyclo[3,2,1]-octan-7-one, prepared as described in Example 3, was dissolved in 50 ml of anhydrous tetrahydrofuran and added to the reaction mixture. The reaction mixture was stood for 1 hour at −78° C. and then quenched with acetic acid. The solvent was removed in vacuo. The residue was purified by silica gel column chromatography, giving 3 g (73% yield) of the title compound. m/z 456 (M+·).

IR (KBr): 1775 $cm^{-1}$ (C=O five membered ring lactone), 1680 $cm^{-1}$ (C=O benzylic ketone).

PMR ($CDCl_3$): inter alia 1.3 (s, $\underline{CH_3}$), 3.75 (s, $OCH_3$), 3.95–4.05 (m, two $O\underline{CH_3}$ and —O—$\underline{CH_2}$—$CH_2$—O—), 6.8 (s, aromatic C$\underline{H}$) and 6.8–8.1 (m, three $\underline{H}$).

EXAMPLE 5

1-(1,4,5-trimethoxy-3-naphthylmethyl-2-benzyloxycarbonyl-4-(1-hydroxyethyl)-4-hydroxy-cyclohexane (XI, R=$OCH_3$)

1.6 g of 2-(1,4,5-trimethoxy-2-naphthylcarbonyl)-5-(2-methyl-dioxolan-2-yl)-6-oxa-bicyclo[3,2,1]octan-7-one, prepared as described in Example 4, was dissolved in methanol and treated at room temperature for 1 hour with a 1N solution of hydrogen chloride in anhydrous methanol. After evaporating off the solvent, there was obtained in almost quantitative yield 1.5 g of 1-1,4,5-trimethoxy-3-naphthylcarbonyl)-2-methoxycarbonyl-4-acetyl-4-hydroxy-cyclohexane (X, R=$OCH_3$). m/z 444 (M+·); IR (film): 3460 $cm^{-1}$ (OH), 1730 $cm^{-1}$ (C=O ester, 1710 $cm^{-1}$ (C=O ketone) and 1665 $cm^{-1}$ (C=O benzylic ketone). PMR ($CDCl_3$): inter alia 2.3 (s, $\underline{CH_3}CO$), 3.75–4.05 (s, four $O\underline{CH_3}$), 6.8 (s, aromatic H) and 6.85–8.0 (m, three aromatic $\underline{H}$). 1.5 g of this compound was dissolved in 15 mo of trifluoroacetic acid and refluxed with 1.4 ml of pyridine-borane complex. After removal of the solvent, the residue was treated with a 10% aqueous solution of sodium hydroxide. After mild acidification the free acid was extracted with ethyl acetate. The solvent was evaporated off and the residue was directly treated with an ethereal solution of phenyldiazomethane to give the title product. This was purified by chromatography: m/z 508 (M+·); PMR ($CDCl_3$): inter alia 1.25 (d, $\underline{CH_3}$—CH), 3.70–3.95 (s, three $O\underline{CH_3}$), 5.15 (d, $\underline{CH_2Ph}$) and 6.4–8.1 (m, nine aromatic $\underline{H}$).

EXAMPLE 6

1,2,3,4,4a,5,12,12a-Octahydro-2-(1-hydroxyethyl)-2-hydroxy-6,7,11-trimethoxy-12-oxonaphthacene (XIII, R=$OCH_3$)

0.48 g of 1-(1,4,5-trimethoxy-3-naphthylmethyl)-2-benzyloxycarbonyl-4-(1-hydroxyethyl)-4-hydroxy-cyclohexane, prepared as described in Example 5, was treated with acetic anhydride and pyridine in the presence of 4-dimethylamino-pyridine. After a night at room temperature the reaction mixture was poured into iced water and extracted with ethyl acetate. The organic layer was washed with water and concentrated. The crude product was dissolved in methanol and refluxed with cyclohexene in the presence of 10% by weight palladium-on-carbon. The catalyst was then filtered off and the solution, concentrated to a small volume, was treated at 0° C. for 60 minutes with trifluoroacetic anhydride and trifluoroacetic acid. Then the solution was diluted with ethyl acetate, washed with an aqueous saturated solution of sodium bicarbonate and with water, dried and concentrated to dryness under vacuum. The residue was dissolved in methanol in the presence of catalytic amount of sodium methylate. After conventional work-up and purification by chromatography 0.18 g of the title compound was obtained (yield 49%): m/z 400 (M+·); IR (KBr): 3450 $cm^{-1}$ (OH), 1675 $cm^{-1}$ (C=O benzylic ketone); PMR ($CDCl_3$): inter alia δ (1.2 (d, $\underline{CH_3}$—CH), 3.7–3.9 (s, three $O\underline{CH_3}$) and 6.4–8.0 (m, three aromatic hydrogen).

EXAMPLE 7

1,2,3,4,4a,5,12,12a-Octahydro-2-acetyl-2-hydroxy-6,7,11-trimethoxy-12-oxo-naphthacene 0.8 g of silver carbonate was added to a solution in benzene of 0.09 g of 1,2,3,4,4a5,12,12a-Octrahydro-2-(1-hydroxyethyl)-2-hydroxy-6,7,11-trimethoxy-12-oxo-naphthacene, prepared as described in Example 6, and the mixture was refluxed. After filtering off the solid and evaporating off the solvent in vacuo, 0.08 g of the title compound was obtained (90% yield).

IR (KBr): 3360 $cm^{-1}$ (OH), 1705 $cm^{-1}$ (C=O ketone), 1680 $cm^{-1}$ (C=O, benzylic ketone).

PMR ($CDCl_3$): inter alia δ 2.2 (s, $CH_3CO$), 3.65–3.90 (s, three $OCH_3$).

EXAMPLE 8

6,7-Dideoxycarminomycinone (XIV, R=OH)

0.06 g of 1,2,3,4,4a,5,12,12a-octahydro-2-acetyl-2-hydroxy-6,7,11-trimethoxy-12-oxonaphthacene, prepared as described in Example 7, was dissolved in nitrobenzene and treated with 0.12 g of aluminium trichloride. The mixture was kept at 70° C. until no more starting material was detectable. The reaction mixture was poured into an aqueous saturated solution of oxalic acid and extracted with ethyl acetate. The organic phase was separated, washed with water, dried and evaporated to dryness. The residue, purified on a column of silica gel, afforded pure 6,7-dideoxycarminomycinone, yield 40%: m/z 352 (M+·); IR (KBr): 3420 $cm^{-1}$ (OH), 1705 $cm^{-1}$ (C=O ketone) and 1625 $cm^{-1}$ (C=O, chelated quinone). PMR ($CDCl_3$): inter alia δ 1.7–2.2 (m, $CH_2$), 2.3 (s, $CH_3CO$), 2.8–3.2 (m, two benzylic $CH_2$), 7.0–7.9 (m, four aromatic H), 12.6 (s, phenolic OH) and 12.9 (s, phenolic OH).

EXAMPLE 9

6-Deoxycarminomycinone (I: R=OH)

A solution of 6,7-dideoxycarminomycinone, prepared as described in Example 8, in benzene was treated at refluxing temperature for 4 hours with 1.2 ml of ethylene glycol in the presence of a catalytic amount of p-toluenesulphonic acid, affording the corresponding 13-ketal derivative. This compound was dissolved in carbon tetrachloride and treated with 2 ml of a solution of 3.2 g of bromine in 32 ml of carbon tetrachloride at 45° C. for 6 hours in the presence of 2,2'-azo-bis-(isobutyronitrile). The cooled reaction mixture was extracted with 1N aqueous sodium hydroxide and the coloured aqueous phase was adjusted to pH 8.5 and extracted with chloroform. The organic extracts, evaporated to dryness, afforded 6-deoxy-13-ketal-carminomycinone. This was dissolved in acetone containing hydrogen chloride (300 ml of a 0.25N solution) and kept at room temperature for 3 hours in order to hydrolyze the ketal group. The desired 6-deoxycarminomycinone was obtained.

Alternative Method

A solution of 50 mg (0.125 mmol) of the 13-ketal derivative of 6,7-dideoxycarminomycinone in 20 ml of carbon tetrachloride containing 0.14 mmol of N-bromosuccinimide and 0.06 mmol of 2,2'-azo-bis(isobutyronitrile) was refluxed for 25 minutes. The residue, obtained by evaporating off the solvent under vacuum was dissolved in glacial acetic acid and treated with 80 mg of silver acetate. The mixture was stirred at room temperature for five hours. The solvent was evaporated off, and the residue was dissolved in ethyl acetate and filtered. The filtrate was washed with a saturated of sodium bicarbonate and with water, dried and concentrated. The residue was dissolved in aqueous acetic (90% by volume) at 0° C. and stirred for 90 minutes. After solvent removal, the residue was dissolved in methanol, sodium methoxide was added and the mixture was stirred for 90 minutes. After neutralization, extraction and washing with water, the residue was purified by flash chromatography with methylene dichloride:acetone (16:1 by volume). The desired 6-deoxycarminomycinome was obtained in 34% overall yield. m/z 368 (M+·), m.p. 211°-213° C., TLC on Kieselgel plates (Merck $F_{254}$) using as eluent solvent toluene:acetone 4:1 by volume, Rf=0.3. PMR (200 MHz, $CDCl_3$): δ 2.1-2.3 (m, 2H, H-8), 2.3 (s, 3H, —$COCH_3$), 2.7-3.1 (q, 2H, H-10), 4.1 (d, 1H, OH-7), 4.4 (s, 1H, OH-9), 4.8 (d, 1H, H-7), 7.3 (d, 1H, H-3), 7.7 (t, 1H, H-2), 7.8 (d, 1H, H-1), 8.1 (s, 1H, H-6), 12.8 (s, 1H, OH-4), 13.2 (s, 1H, OH-11).

EXAMPLE 10

2-(1,4-Dimethoxy-3-naphthylcarbonyl)-5-(2-methyl-dioxolan-2-yl)-6-oxa-bicyclo[3,2,1]octan-7-one (IX, R=H)

Following the method described in Example 4, a solution of 3.2 g of 1,4-dimethoxy-3-bromo-naphthalene in anhydrous tetrahydrofuran was treated at −78° C. with n-butyllithium and then added to a solution in anhydrous tetrahydrofuran of 2.7 g of the compound prepared in Example 3. After silica gel column purification 2.8 g of the title compound was obtained (65% yield) m/z 426 (M+·): IR (film): 1780 $cm^{-1}$ (C═O, five membered ring lactone), 1670 $cm^{-1}$ (C═O, benzylic ketone); PMR ($CDCl_3$): inter alia: δ 1.4 (s, $CH_3$), 3.85 (s, two $OCH_3$), 3.9 (s, —O—$CH_2$—$CH_2$—O—), 6.9 (s, aromatic H) and 7.4-8.4 (m, four aromatic H).

EXAMPLE 11

1-(1,4-dimethoxy-3-naphthylmethyl)-2-benzyloxycarbonyl-4-(1-hydroxyethyl)-4-hydroxy-cyclohexane (XI, R=H)

Operating as described in Example 5, the treatment of 2-(1,4-dimethoxy-3-naphthylcarbon)-5-(2-methyl-dioxolan-2-yl)-6-oxa-bicyclo[3,2,1]octan-7-one, prepared as described in Example 10, with a solution of hydrogen chloride in methanol afforded 1-(1,4-dimethoxy-3-naphthylcarbonyl)-2-methoxycarbonyl-4-acetyl-4-hydroxy-cyclohexane (X, R=H) in almost quantitative yield. m/z 414 (M+·): IR (film): 3460 $cm^{-1}$ (OH), 1730 $cm^{-1}$ (C═O ester), 1710 $cm^{-1}$ (C═O ketone) and 1670 $cm^{-1}$ (C═O, benzylic ketone). PMR ($CDCl_3$): inter alia: δ 2.3 (s, $CH_3CO$), 2.9-3.6 (m, two H), 3.7-3.9 (s, three $OCH_3$), 6.9 (s, aromatic H) and 7.4-8.4 (m, four aromatic H).

1 g of this compound, by reduction with pyridine-borane complex, basic treatment and finally esterification with phenyldiazomethane was converted to the title compound (0.7 g, overall yield 63%). m/z 478 (M+·): IR (film): 3450 $cm^{-1}$ (OH), 1725 $cm^{-1}$ (C═O, ester). PMR ($CDCl_3$): inter alia δ 1.3 (d, J=4 Hz, $CH_3$—CH), 3.85-3.9 (s, two $OCH_3$), 5.1 (s, $CH_2$-benzylic), 6.6 (s, aromatic H) and 7.2-8.4 (m, nine aromatic hydrogens).

EXAMPLE 12

1,2,3,4,4a,5,12,12a-Octahydro-2-(1-hydroxyethyl)-2-hydroxy-6,11-dimethoxy-12-oxo-naphthacene (XIII, R=H)

Operation as described in Example 6, 0.44 g of 1-(1,4-dimethoxy-3-naphthylmethyl)-2-benzyloxycarbonyl-4-(1-hydroxyethyl)-4-hydroxyl-cyclohexane, prepared as described in Example 11, was treated with acetic anhydride in presence of 4-dimethylamino-pyridine and pyridine. The corresponding acetate was treated with cyclohexene in the presence of 10% by weight palladium-on-carbon in order to remove the benzyl group. The acid was cyclized by treatment with a mixture of trifluoroacetic anhydride and trifluoroacetic acid at 0° C. Finally the removal of the acetyl O-protecting groups by treatment with sodium methylate afforded. after purification by chromatography on a silica gel column, 0.225 g of the title compound (overall yield 66%); IR (film): 3450 $cm^{-1}$ (OH), 1675 $cm^{-1}$ (C═O, benzylic ketone). PMR ($CDCl_3$): inter alia δ 1.3 (d, J=4 Hz, $CH_3$—CH), 1.6-3.5 (m, 3H), 3.85 (s, $OCH_3$), 3.90 (s, $OCH_3$), 7.2-8.4 (m, four aromatic H).

EXAMPLE 13

1,2,3,4,4a,5,12,12a-Octahydro-2-acetyl-2-hydroxy-6,11-dimethoxy-12-oxo-naphthacene 0.1 g of 1,2,3,4,4a,5,12,12a-octahydro-2-(1-hydroxyethyl)-2-hydroxy-6,11-dimethoxy-12-oxo-naphthacene, prepared as described in Example 12, in benzene was treated with 1 g of silver carbonate at refluxing temperature. After filtering off the inorganic solids and removing the solvent, 0.1 g of the title product was obtained.

IR (film): 3460 $cm^{-1}$ (OH), 1710 $cm^{-1}$ (C═O ketone), 1680 $cm^{-1}$ (C═O benzylic ketone).

PMR ($CDCl_3$): inter alia δ 2.4 (s, $CH_3CO$), 3.85 (s, $OCH_3$), 3.90 (s, $OCH_3$), 7.2-8.4 (m, four aromatic H).

EXAMPLE 14

4-Demethoxy-6,7-dideoxydaunomycinone (XIV, R=H)

Operating as described in Example 8, a solution of 0.1 g of 1,2,3,4,4a,5,12,12a-octahydro-2-acetyl-2-hydroxy-6,11-dimethoxy-12-oxo-naphthacene, prepared as described in Example 13, in 3 ml of nitrobenzene was treated with 0.25 g of aluminium trichloride overnight at room temperature. After silica gel column chromatography, 0.055 g (63% yield) of the title compound was obtained. m.p. 203°-204° C.

EXAMPLE 15

6-Deoxy-4-demethyl daunorubicin (XVb)

90 mg (0.24 mmol) of racemic 6-deoxy-carminomycinone, prepared as described in Example 9 was dissolved in anhydrous dichloromethane and the solution was cooled to 5°-10° C. A solution of 2.4 mg (0.6 mmol) of 1-chloro-N,O-ditrifluoroacetyl-daunosamine, prepared following the procedure described in Cancer Chemotherapy Reports, Part 3, Vol. 6, No. 2, p. 123, in diethyl ether and a solution of 154 mg (0.6 mmol) of silver trifluoromethanesulphonate in dichloromethane were added simultaneously and rapidly under vigorous stirring.

After 5 minutes, a further 0.3 mmol of the halosugar and 0.3 mmol of silver trifluoromethane sulphonate were added. After 5 minutes, the reaction was quenched with collidine. The mixture was filtered, washed with a saturated aqueous solution of sodium bicarbonate and with water, dried and concentrated under vacuum. The reddish oil obtained was diluted with 100 ml of methanol and allowed to stand overnight at room temperature to remove the O-trifluoroacetyl group. The resulting crude product was purified by flash chromatography on silica gel with dichloromethane:methanol:acetone 20:1:1 by volume to afford the anthracycline α-glycosides XVa. 7S:9S, 20 mg, m.p. 210°-212° C.

TLC on kieselgel plates (Merck $F_{254}$), using as eluent methylene-dichloride:acetone 4:1 by volume, Rf=0.27. m/z 593 ($M^{+\cdot}$).

PMP (2000 MHz, $CDCl_3$): inter alia δ 1.44 (d, J=6.6 Hz, 3H, $CH_3$-5'), 2.42 (s, 3H, $COCH_3$), 3.25-3.05 (two d, J=19 Hz, 2H, H-10), 4.22 (s, 1H, OH-9), 5.01 (t, J=3.6 Hz, 1H, H-7), 5.20 (t, J=2.7 Hz, 1H, H-1'), 6.66 (bd, J=9 Hz, 1H, NH), 7.80 (s, 1H, H-6), 12.62 (s, 1H, OH-4), 13.06 (s, 1H, OH-11); m/z 593 ($M^{+\cdot}$), 7R:9R 25 mg, m.p. 174°-178° C.

TLC on kieselgel plates (Merck $F_{254}$) using as eluent methylene dichloride:acetone 4:1 by volume, Rf=0.23. m/z 593 ($M^{+\cdot}$).

PMR (200 MHz, $CDCl_3$): inter alia δ 1.44 (d, J=6.5 Hz, 3H, $CH_3$-5'), 2,41 (s, 3H, $COCH_3$), 2.96 (d, J=19 Hz, 1H, H-10 ax), 3.30 (dd, J=1, 19 Hz, 1H, H-10 eq), 4.25 (x, 1H, OH-9), 5.07 (t, J=3.3 Hz, 1H, H-7), 5.27 (t, J=1.8 Hz, 1H, H-1'), 6.64 (bd, J=9 Hz, 1H, NH), 7.74 (s, 1H, H-6), 12.66 (s, 1H, OH-4), 13.10 (s, 1H, OH-11).

Mild alkaline hydrolysis of XVa removes the N-trifluoroacetyl group to give the title compound in quantitative yield. TLC on kieselgel plates (Merck $F_{254}$) using as eluent methylene dichloride:methanol:acetic acid:-water 80:20:7:3 by volume, Rf 0.47.

EXAMPLE 16

6-deoxy-4-demethyl-doxorubicin (XVc)

A solution of 6-deoxy-4-demethyl-daunorubicin prepared as described in Example 15 in a mixture of methanol and dioxane was treated with bromide to form the 14-bromo derivative. Treatment of the 14-bromo derivative with an aqueous solution of sodium formate at room temperature for 100 hours gave 6-deoxy-4-demethyl-doxorubicin.

m.p. 167°-170° C.

Chromatography on TLC (Merck F254) using solvent system $CH_2Cl_2$:MeOH:AcOH:$H_2O$ (8:2:0.7:0.3 v/v) Rf=0.47.

What we claim is:

1. 4-demethyl-6deoxy-daunomycinone.

2. 6-deoxy-daunomycinone.

* * * * *